US010271817B2

United States Patent
Voigt et al.

(10) Patent No.: US 10,271,817 B2
(45) Date of Patent: Apr. 30, 2019

(54) VALVE REGURGITANT DETECTION FOR ECHOCARDIOGRAPHY

(71) Applicant: Siemens Medical Solutions USA, Inc., Malven, PA (US)

(72) Inventors: Ingmar Voigt, Erlangen (DE); Tommaso Mansi, Plainsboro, NJ (US); Bogdan Georgescu, Plainsboro, NJ (US); Helene C Houle, San Jose, CA (US); Dorin Comaniciu, Princeton Junction, NJ (US); Codruta-Xenia Ene, Prahova (RO); Mihai Scutaru, Brasov (RO)

(73) Assignee: Siemens Medical Solutions USA, Inc., Malvern, PA (US)

( * ) Notice: Subject to any disclaimer, the term of this patent is extended or adjusted under 35 U.S.C. 154(b) by 299 days.

(21) Appl. No.: 14/735,203

(22) Filed: Jun. 10, 2015

(65) Prior Publication Data
US 2015/0366532 A1    Dec. 24, 2015

Related U.S. Application Data

(60) Provisional application No. 62/015,671, filed on Jun. 23, 2014.

(51) Int. Cl.
*A61B 8/06*    (2006.01)
*A61B 8/00*    (2006.01)
(Continued)

(52) U.S. Cl.
CPC ............ *A61B 8/065* (2013.01); *A61B 8/0883* (2013.01); *A61B 8/14* (2013.01); *A61B 8/463* (2013.01);
(Continued)

(58) Field of Classification Search
CPC ......... A61B 8/065; A61B 8/5223; A61B 8/02; A61B 8/0883; A61B 8/12; A61B 8/14;
(Continued)

(56) References Cited

U.S. PATENT DOCUMENTS 8,771,189 B2    7/2014    Ionasec et al.
9,033,887 B2    5/2015    Ionasec et al.
(Continued)

OTHER PUBLICATIONS

Thavendiranathan et al., "Quantitative Assessment of Mitral Regurgitation" JACC: Cardiovascular Imaging. 2012. vol. 5, No. 11, 1161-1175.*
(Continued)

*Primary Examiner* — Katherine L Fernandez
*Assistant Examiner* — Yi-Shan Yang

(57) ABSTRACT

A regurgitant orifice of a valve is detected. The valve is detected from ultrasound data. An anatomical model of the valve is fit to the ultrasound data. This anatomical model may be used in various ways to assist in valvular assessment. The model may define anatomical locations about which data is sampled for quantification. The model may assist in detection of the regurgitant orifice using both B-mode and color Doppler flow data with visualization without the jet. Segmentation of a regurgitant jet for the orifice may be constrained by the model. Dynamic information may be determined based on the modeling of the valve over time.

16 Claims, 4 Drawing Sheets

(51) Int. Cl.
         A61B 8/08       (2006.01)
         A61B 8/14       (2006.01)
         G06T 7/00       (2017.01)
         G06T 19/00      (2011.01)
         A61B 8/12       (2006.01)
(52) U.S. Cl.
     CPC ............ *A61B 8/488* (2013.01); *A61B 8/5223*
            (2013.01); *A61B 8/5238* (2013.01); *G06T
            7/0012* (2013.01); *G06T 19/00* (2013.01);
            *A61B 8/12* (2013.01); *G06T 2207/10132*
            (2013.01); *G06T 2207/20081* (2013.01); *G06T
            2207/30048* (2013.01); *G06T 2210/41*
                                                    (2013.01)
(58) Field of Classification Search
     CPC ....... A61B 8/463; A61B 8/488; A61B 8/5238;
                 A61B 8/565; A61B 8/0012; G06T 19/12;
                 G06T 2207/10132; G06T 2207/20081;
                 G06T 2207/33048; G06T 2210/41
     See application file for complete search history.

(56)              References Cited

U.S. PATENT DOCUMENTS

2005/0165308 A1*   7/2005   Jacob ................. A61B 8/06
                                                      600/443
2013/0144161 A1*   6/2013   Wang ................. A61B 8/065
                                                      600/438

OTHER PUBLICATIONS

Grady et al., "Regurgitation Quantification Using 3D PISA in Volume Exhocardiography". MICCAI 2011, Part III, LNCS 6893, pp. 512-519.*

Wang et al., "Automatic Detection and Quantification of Mitral Regurgitation on TTE with Application to Assist Mitral Clip Planning and Evaluation". Clinical Image-Based Procedures (CLIP), 2012, pp. 33-41 (Conference @2012, publication in CLIP in Jan. 2013 (see p. IV, preface).*
Grady, Leo, et al. "Regurgitation quantification using 3D PISA in voulme echocardiography." Medical Image Computing and Computer-Assisted Intervention—MICCAI 2011. Springer Berlin Heidelberg, 2011. pp. 512-519.
Mahmood, Feroze, et al. "Intraoperative application of geometric three-dimensional mitral valve assessment package: a feasibility study." Journal of cardiothoracic and vascular anesthesia vol. 22 No. 2, (2008): pp. 292-298. (Abstract Only).
Mansi, T., Voigt, I., Mengue, E.A., Ionasec, R., Georgescu, B., Noack, T., Seeburger, J., Comaniciu, D.: Towards patient-specific finite-element simulation of mitralcfip procedure. In: MICCAI. vol. 1. (2011) 452-459.
Veronesi, F., Corsi, C., Caiani, E., Sugeng, L., Weinert, L., Mor-Avi, V., Lang, R., Lamberti, C: Semi-automatic tracking for mitral annulus dynamic analysis using real-time 30 echocardiography. In: Computers in Cardiology. (2006) 113-116.
Schneider, R.J., Tenenholtz, N. A., Perrin, D.P., Marx, G.R., del Nido, P.J., Howe, R.D.: Patient-specific mitral leafle segmentation from 40 ultrasound. In: MICCAI. (2011) 520-527.
Ionasec, R.I., Voigt, I., Georgescu, B., Wang, Y., Houle, H., Vega-Higuera, F., Navab, N., Comaniciu, D.: Patient-specific modeling and quantification of the aortic and mitral valves from 40 cardiac CT and TEE In: TMI. (2010) 1636-1651.
Burlina, Philippe, et al. "Patient-specific modeling and analysis of the mitral valve using 3D-TEE."Information Processing in Computer-Assisted Interventions. Springer Berlin Heidelberg, 2010. 135-146.
Wenk, Jonathan F., et al. "First finite element model of the left ventricle with mitral valve: insights into ischemic mitral regurgitation." The Annals of thoracic surgery89.5 (2010): 1546-1553.

* cited by examiner

VALVE REGURGITANT DETECTION FOR ECHOCARDIOGRAPHY

RELATED APPLICATIONS

The present patent document claims the benefit of the filing dates under 35 U.S.C. § 119(e) of Provisional U.S. Patent Application Ser. No. 62/015,671, filed Jun. 23, 2014, which is hereby incorporated by reference.

BACKGROUND

The present embodiments relate to detecting a regurgitant orifice. In particular, the regurgitant orifice is detected from medical scan data. The present embodiments also relate to refining the detection of valve anatomy according to the detected regurgitant orifice.

Valvular heart diseases are a major cause of death in developed countries. In 2006 in the United States, valvular heart diseases are estimated to affect 2.5% of the population and are the underlying cause of over 43,700 deaths and 93,000 hospital discharges. Pooled data from multiple studies suggest that the prevalence increases with age from 0.7% in participants 18-44 years of age to 13.3% in participants >=75 years of age.

Stenosis and regurgitation impair transvalvular blood flow and reduced cardiac function. Specifically, stenoses reduce the transvalvular flow through a narrowing of the heart valve as opposed to regurgitation, where the valve is rendered incompetent by insufficient closure. This insufficient closure allows for pathologic reverse flow. Treatments include medication, or repair or replacement via open-heart surgery or implants delivered via catheters or minimally invasive instruments.

Valve competency is routinely assessed using quantitative and qualitative information both from anatomy and blood flow shown in four-dimensional (3D+time) B-Mode and Color Doppler obtained using transthoracic (TTE) and transesophageal (TEE) echocardiography. Four-dimensional imaging enables more accurate non-invasive assessment as compared to two-dimensional echocardiography. Four-dimensional imaging allows quantification with anatomical dimensions and hemodynamic biomarkers, such as proximal isosurface velocity area (PISA) and effective regurgitant orifice area (EROA). While these biomarkers are widely accepted, the quantities are derived manually. The amount of information to be processed manually is large with four-dimensional imaging. Due to manual calculation, inter- and intra-observer variation results.

Moreover, 3D B-Mode imaging is not able to capture regurgitant orifice area. Hence, color Doppler imaging is used to find the location of regurgitant jets. Rendering both 3D B-Mode and color Doppler flow images together still may not show the regurgitant orifice since the color overlay often obscures the view onto the valve.

BRIEF SUMMARY

By way of introduction, the preferred embodiments described below include methods, computer readable media, and systems for detecting a regurgitant orifice. The valve is detected from ultrasound data. An anatomical model of the valve is fit to the ultrasound data. This anatomical model may be used in various ways to assist in valvular assessment. The model may define anatomical locations about which data is sampled for quantification. The model may assist in detection of the regurgitant orifice using both B-mode and color Doppler flow data with visualization without the jet. Segmentation of a regurgitant jet for the orifice may be constrained by the model. Dynamic information may be determined based on the modeling of the valve over time.

In a first aspect, a method is provided for detecting a regurgitant point in echocardiography. A processor detects a valve with a first machine-learnt classifier using input first features from both B-mode and flow-mode data for a patient. The processor fits a model of the valve to the detected valve of the patient and detects the regurgitant point with a second machine-learnt classifier using second features from both the B-mode and the flow-mode data. The second machine-learnt classifier is applied based on the model as fit to the valve. The processor segments a regurgitant jet based on the regurgitant point. An image or quantity is output. The detected regurgitant jet can also be applied to refine the model of the valve, in particular the free-edges (e.g., if no jet is detected, the model of the valve is forced to be closed since no insufficiency is present, and if a jet is detected, the model of the valve is forced to be open).

In a second aspect, a non-transitory computer readable storage medium has stored therein data representing instructions executable by a programmed processor for detecting a regurgitant orifice. The storage medium includes instructions for detecting, at different times, anatomy of a heart valve from first features derived from both B-mode and color flow Doppler data, sampling, at the different times, transvalvular flow over time from the color flow Doppler data on sampling planes positioned relative to the detected heart valves for the different times, calculating a quantity of transvalvular flow from the sampling, detecting the regurgitant orifice from second features from the color flow Doppler data and from the B-mode data, the detecting of the regurgitant orifice being a function of an anatomical model for the detected anatomy, segmenting a regurgitant jet for the heart valve based on the regurgitant orifice, and computing a clinical biomarker for the regurgitant jet.

In a third aspect, a system is provided for detecting a regurgitant region. An ultrasound scanner is configured to scan a heart volume of a patient, the scan providing B-mode and Doppler flow data. A processor is configured to fit a model of a heart valve over time to the B-mode data using the B-mode data and the Doppler flow data and use the model to locate a regurgitant region over time. A display is configured to generate a visualization of the model over time and highlight the regurgitant region without displaying a regurgitant jet.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Integrated assessment of valve anatomy and physiology uses both B-mode and color Doppler sonography. Models and biomarkers of anatomy and physiology are automatically estimated by applying learning-based methods on both B-mode and color Doppler data. A processor detects and tracks anatomy and dynamics of heart valves from using multi-channel image features derived both B-mode and color flow Doppler images. Transvalvular flow is sampled and quantified over time by deriving sampling planes from valve anatomy over the cardiac cycle. Regurgitant areas are detected and tracked by integrating features from anatomical models and multi-channel image features. The processor segments, tracks, and quantifies in four dimensions for regurgitant jets over systole for mitral and diastole for aortic valves. Previously tracked regurgitant areas are used to compute clinical biomarkers for valve regurgitations.

The valve model estimation is integrated to assist in assessment. Any types of scans (e.g., TTE or TEE) may be used for any type of valve (e.g., aortic, mitral, pulmonary, or tricuspid). Dynamics (i.e., tracking over time) are included for computing dynamic flow measurements. Since a model is fit to the scan data, the complete or any valve anatomy may be included for visualization. In some embodiments, only the valve model detected regurgitant orifice is displayed for a better view and surgical planning. The regurgitant jet is segmented out and not displayed, at least for an image.

Accurate anatomical models result from using both B-mode and color Doppler flow data for anatomy delineation. Accurate flow quantification may use sampling planes derived from valve anatomy of the model. Detection of regurgitant area on the valve is enhanced by leveraging anatomical models in addition to multi-channel features (e.g., jet location always located on the valve). 3D+time biomarker quantification (e.g., velocity time integral (VTI) and/or regurgitant volume) is enabled by tracking the regurgitant orifice over time.

A single holistic and consistent workflow may be applied for both TTE and TEE throughout the whole clinical workflow. In diagnosis and monitoring, TTE is used for early detection and intervention decision. For intervention and follow up, pre, intra, or post (e.g., immediate) operative TEE examinations support assessment of outcome and decisions for additional measures. These assessments are supported quantitatively and qualitatively. Measurements of valvular anatomy and transvalvular flow are provided. Overall cardiac performance is indicated by integrating several biomarkers, including but not limited to stroke volume, ejection fraction, PISA, EROA, VTI, and/or regurgitant volume, by including a temporal dimension. Pathology via anatomy and regurgitant jet (e.g., for surgical planning of mitral leaflet resection) is visualized without occluding the anatomical view with flow rendering.

Figure 1:
FIG. 1 shows from left to right example B-mode and flow mode images and an example fitted model image of the mitral valve.

The left and center images of FIG. 1 show B-mode and Doppler velocity images. The valve may be shown in the images, but is not very distinct or is difficult to locate. To assist the sonographer, the valve or valve anatomy may be detected and highlighted, such as shown in the right image of FIG. 1. In the center image, two versions are provided. In the right most version, a segmented 3D proximal iso-velocity surface area (3D PISA) is shown.

For automatic detection, 3D features are computed on multiple channels, including the volumetric anatomical (B-Mode) and hemodynamical (color Doppler or flow) channels, to extract both morphological and functional information. Based on the extracted multi-channel features, a discriminative classifier is then trained through a boosting process to detect the valve and/or regurgitant orifice. In order to locate the associated valve structure, such as the valve annulus and the valve closure line, a statistical shape model is further integrated into the framework. This model is used to assist in regurgitant orifice detection, dynamic quantification, and/or segmentation.

Figure 2:
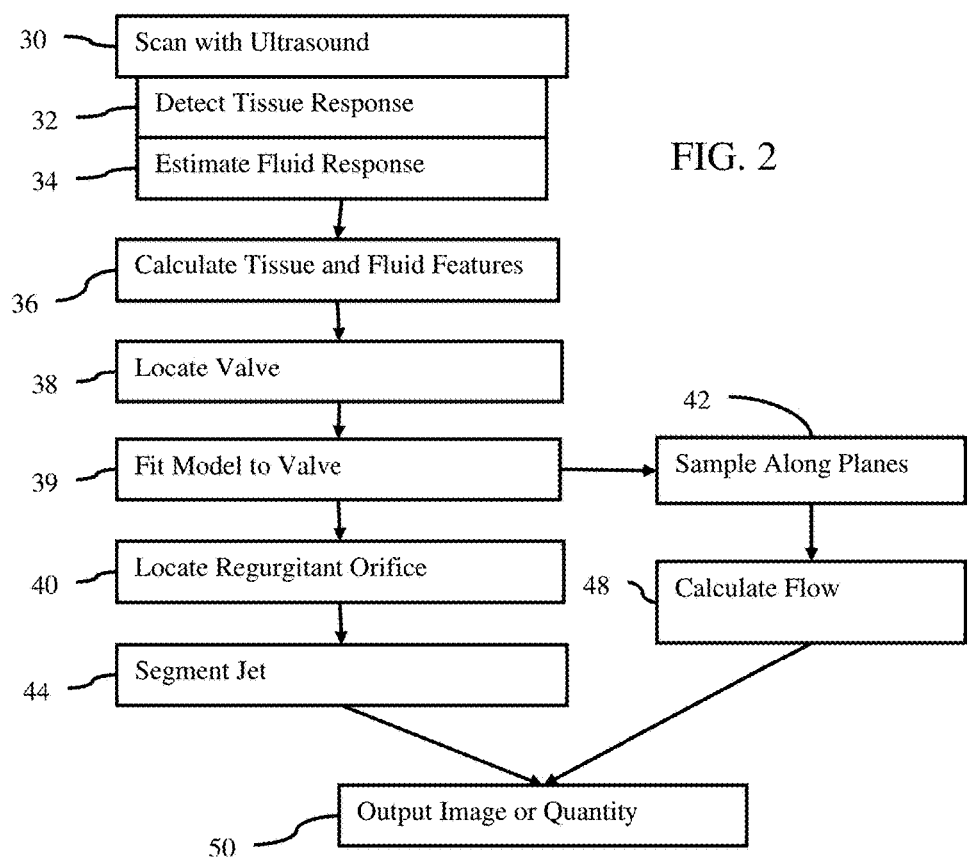
FIG. 2 is a flow chart diagram of one embodiment of a method for detecting a regurgitant orifice in echocardiography.

FIG. 2 shows a method for detecting a regurgitant orifice in echocardiography. The method is implemented by a medical diagnostic imaging system, a review station, a workstation, a computer, a PACS station, a server, combinations thereof, or other device for image processing medical diagnostic data. For example, the system or computer readable media shown in FIG. 6 implements the method, but other systems may be used. A processor performs the various detection, computation, segmentation, and fitting acts. An ultrasound scanner performs the scanning, estimating, and B-mode detection acts.

The method is implemented in the order shown or a different order. For example, acts 40 and 44 may be performed prior to, after, or simultaneously with acts 42 and 48. Additional, different, or fewer acts may be performed. For example, one or more of acts 30-34 are not provided where the ultrasound data is loaded from memory. As another example, acts 40, 44, and/or 48 are not performed. In yet another example, act 50 is not provided where image or quantity information is stored or transferred.

The acts are performed in real-time, such as during ultrasound scanning of act 30. The user may view images of act 50 while scanning in act 30 to acquire another dataset representing the cardiac volume. The acts may be performed during an appointment or off-line in a review period. The images may be associated with previous performance of one or more of the acts in the same imaging session. Measurements and/or images of automatically detected anatomy may be provided in seconds, such as ten or fewer seconds. Alternatively, the acts are performed as desired by a surgeon regardless of whether a patient is currently at the facility or being scanned.

The acts are performed for diagnosis, planning, or other purpose. In one embodiment, the acts are performed prior to a mitral clipping or other repair procedure to assist in planning the procedure. The acts may be repeated or alternatively performed after the procedure to evaluate results of the procedure. Mitral regurgitation quantification provides pre and post MitraClip or other procedure measures. The average mitral regurgitation volume after a MitraClip procedure may be reduced compared to the pre-procedure value, confirming a good clinical outcome.

A processor, such as associated with a computer, server, or dedicated detector, performs acts 36-50. The acts 36-50 are performed without further user input. The user may activate the process, such as configuring an ultrasound system for valve detection and activating the process. The user may shift the transducer until images show the cardiac region likely to include the valve, but the user does not indicate a location of the valve on the images. The processor automatically identifies the valve, valve anatomy, and/or regurgitant orifice without user input other than activation and scanning position. The user does not indicate the location of the valve within the cardiac region. In alternative embodiments, a semi-automatic process is used where the user confirms or guides the process by indicating one or more locations and/or indicating changes due to proposed treatment.

In act 30, a cardiac region of a patient is scanned with ultrasound. An ultrasound transducer, such as an array of 32, 64, 128, 256 or other number of elements, is positioned against the patient. For transthoracic echocardiography, the transducer is positioned on the chest of the patient such that the acoustic energy passes between ribs of the patient to scan the heart or portion of the heart. For transesophageal echocardiography, the transducer is positioned in an esophagus of the patient such that the acoustic energy scans the heart. A handheld or machine positioned probe is used on the skin surface or in the esophagus of the patient. Other types of ultrasound imaging may be used, such as cardiac catheter ultrasound imaging.

Any format for scanning may be used, such as linear, sector, Vector®, or other format. The distribution of scan lines is in three-dimensions to scan a volume of the cardiac region. The volume is scanned using electronic and/or mechanical steering (e.g., wobbler array). The transducer is held in place or moved to scan the volume.

The scanning transmits acoustic energy. In response to the transmissions, acoustic echoes are received. Different structures or types of structures react to the acoustic energy differently. Using beamforming, the cardiac region is sampled. For rapid volume scanning, plane wave or broad transmit beams are formed. Multiple, such as 4, 8, 16, 32, 64, or other number, of receive beams are formed in response to each transmit beam. In alternative or additional embodiments, cardiac or ECG gating is used to scan in synchronization with the cardiac cycle. Transmissions and receptions from different cycles but at the same time relative to the cycle may be combined to sample the cardiac region. For dynamic assessment, the patient is repetitively scanned throughout the heart cycle.

For patient specific modeling, sets of data are obtained by scanning. The sets represent the cardiac region at different periods or phases of the cardiac cycle. Sets of data representing the volume multiple times during a heart cycle are acquired by scanning. The ultrasound data corresponds to a data set interpolated to a regular 3D grid, displayed images (e.g., detected and scan converted ultrasound data), beamformed data, detected data, and/or scan converted data. The ultrasound data represents the volume or 3D cardiac region of the patient. The region includes tissue, fluid or other structures.

In act 32, the tissue response to the acoustic energy is detected. The receive beamformed samples are processed to represent the intensity of the echoes from the location. B-mode detection is performed. The B-mode data represents the tissue in the cardiac region. Using thresholding and/or filtering, signals associated with fluid are removed. Since the intensity of return from fluid is relatively small, B-mode data may include little or no signal from fluid. The distribution of B-mode data shows the shape of a structure or spatial aspect. The B-mode data is of the echoes at a fundamental (transmit) frequency or a harmonic thereof (e.g., second harmonic). In alternative embodiments, Doppler tissue imaging or other mode is used to detect the tissue response.

In act 34, fluid response to the acoustic energy is estimated. Flow data representing the fluid in the cardiac region is estimated. Since fluid is typically moving, the change associated with the movement may be used to represent the flow. Doppler processing, whether relying on the Doppler phenomena or based on other ultrasound processing, estimates the flow data. A shift in frequency may be used to estimate the energy, velocity, variance, or combinations thereof of the fluid. For example, the Doppler velocity is estimated as a velocity value or the shift frequency. Other flow estimation may be used, such as determining motion between samples from different times using correlation. Any flow-mode estimation may be used, such as color Doppler flow.

In alternative embodiments, the B-mode or tissue response data and the flow mode or fluid response data are acquired from a memory. Previously acquired information is loaded or received for further processing to detect the valve.

In act 36, a valve is detected. While the valve is a tissue structure, flow around the valve may be distinctive or indicate the location of the valve. A machine-learnt classifier uses input features from both the B-mode and flow-mode data of the patient to detect the representations of the valve of the patient. Any valve is detected, such as the aortic, mitral, pulmonary, or tricuspid valves. The detection is of the overall valve anatomy or of specific anatomy of the valve, such as the annulus, leaflets, root, free edge, outflow track, or other landmarks.

The valve or valve anatomy are detected for each frame of volume data or time. By repeating the detection, the valve or valve anatomy are found through a sequence of frames or over time, such as over one or more heart cycles.

In one embodiment, the valve or anatomy is detected over time using multi-channel image features from both B-Mode and Color Doppler. The detection may search only a sub-set of locations or voxels since anatomy (i.e., tissue) cannot spatially coincide with the color Doppler signal (i.e., blood pool). The detection is applied to just the tissue locations and not the flow locations. The detection is constrained to locations without flow-mode data.

The valve anatomy is detected directly. The classifier is applied to the data to locate the valve anatomy. The location or locations with the greatest probability are selected. In other embodiments, a bounding box is first detected. While the bounding box does not exist as anatomy, the classifier may be trained to locate a rectangular prism or other shape surrounding the likely locations of the valve anatomy. The more computationally expensive classifier for detecting the valve anatomy is then applied just within the detected boundary box.

To detect the valve and/or boundary box, tissue and fluid features are calculated. The features are not specific cardiac, valve anatomy or jet features, but are features for input to a classifier. Anatomy or jet features may be used as input features for the classifier. Other features, such as the B-mode data and flow data or values derived there from, may be used.

The feature values for input to the classifier are calculated from both the B-mode data and the flow data. A given feature value may be derived from just B-mode or just flow data. For classification, input features from both the B-mode data and the flow data are input. A set of B-mode features is input, and a set of flow data features are input. In alternative or additional embodiments, a given input feature is a function (e.g., sum) of both types of data. In other embodiments, only B-mode or only flow mode data is used. Additional features, such as features not from scanning or images, may be used as well.

In order to extract both morphological and functional information, 3D features are computed for these multiple channels. 2D, 1D, or point features may be used.

Any type of input features may be calculated. For example, gradients of the data, the data itself, detected anatomical or jet features of the data, maximum, minimum, other statistical, or other information are calculated from the B-mode and flow data. In one embodiment, 3D Haar wavelets and steerable features are used. These features are relatively fast to compute and capture information well.

Flow data is on a different scale than B-mode data. For example, the B-mode data has a 0-255 scale of possible intensities. Flow data is signed to represent flow to and away from the transducer. The range of the scale may be different such as −100 to 100. The input features may be calculated using the native scales. Alternatively, the feature values or the data used to calculate the feature values are scaled to compensate for the scale differences. For example, the flow data is transformed to the B-mode scale to have a same range. Other dynamic range adjustment may be used. The B-mode data may be transformed to the flow data scale or both may be transformed to a common scale.

In one embodiment, the global valve anatomy is localized. A position, orientation, and/or scale of the valve region or bounding box within the cardiac or scan region is located. The global valve anatomy is the entire valve or a portion of the valve without being a specific part and/or with being a collection of multiple parts. The valve as distinguished from heart wall, other valves, or other heart anatomy is located.

A bounding box, sphere, segmented surface, or other shape is used to designate the global valve anatomy. In one embodiment, the global location of the valve anatomy is represented by a bounding box parameterized with an affine transformation. The bounding box θ is parameterized for translation T (position), rotation R (a), and scale S along the three dimensions of the volume. Other parameterizations may be used, such as with just translation and rotation (not scale) or with one or more aspects limited to fewer than three dimensions.

In this representation, the position of the bounding box is given by the barycenter of the valve. Other indications of position, such as a corner of the box, may be used. The scale is chosen to enclose the entire underlying valve anatomy. The shape or scale may include other information, such as including tissue from adjacent structures of the heart and/or part or all of the regurgitant jet. The orientation is defined by the trigonal plane. Other references for scale and/or orientation may be used.

The global valve anatomy, such as represented by the bounding box, is located using some or all of the input features. Different features may be used for different classifiers. The tissue ultrasound features derived from B-mode data and the flow ultrasound features derived from Doppler data (e.g., derived from velocity) are used to locate the valve. Some features may be more determinative of location, rotation, and/or scale than others. Some features may not be used for global localization. Since the view angle and other scan parameters may vary from scan to scan, all of the calculated input features may be used.

The global position of the valve is located by a classifier. The feature values are input to the classifier, and the classifier outputs the bounding box, parameter values, or other indicator of the global position of the valve. The classifier is a machine-learnt classifier. Based on the extracted 3D multi-channel features, a discriminative classifier or classifiers are trained to detect the location of the valve.

Other discriminative classifiers may be used for other detections, such as for locating the valve more explicitly or for detecting the regurgitant orifice. To achieve robust and accurate detection results, the search is performed in a hierarchical manner. The global location of the valve anatomy uses one classifier, followed by the estimation of valve anatomy, and then following by the regurgitant orifice. The same or different types of classifiers may be used. Since the classifiers are used for different purposes, the resulting machine-learnt classifier for one stage is different than for another stage even if using a same type.

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, tens or hundreds of volume sequences representing the heart and including the valve are annotated. The annotation indicates valve landmarks, global locations, surfaces, or other relevant information within the volumes. The anatomies of each volume are annotated. This large number of annotations allows use of a probabilistic boosting tree to learn relevant features over a large pool of 3-D Haar, steerable features, and/or other features. Each classifier uses the data sets and annotations specific to the anatomy or box being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the anatomies and/or measurement indicators for the anatomies. The detectors are trained on a large number of annotated 3D volumes. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different times, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features.

A tree structure may be learned and may offer efficiency in both training and application. Often, in the midst of boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques.

In one embodiment of the classifier for global valve localization, a marginal space learnt classifier is applied. The global region is located in stages or with sequentially determined translation, rotation, and scale along three-dimensions. The position within the volume is first classified, and then the rotation at that position is classified, followed by the scale given the position and rotation. The machine-learned matrix finds position candidates around the valve based on Haar and steerable features. The position candidates are then successively refined by rotation and scaling candidates. This defines a region of interest for the valve, such as the bounding box.

The bounding box or valve region detection is used to specifically detect the valve or valve anatomy. Further classification by another machine-trained classifier is used to detect the location, orientation, and/or scale of the valve or valve anatomy as represented by the ultrasound data. The bounding box or region detection is used to limit the search for the valve anatomy. Alternatively, the first stage of classification is to detect the valve anatomy without first detecting the bounding box.

The valve is detected by detecting the whole structure and/or by detecting specific landmarks or parts of the valve. The anatomy of the valve is identified in the data. For example, the annulus and/or closure line are identified. In other examples, other anatomies, such as leaflets and/or chordae, are identified. Any part of the valve may be located. Given the identified valve region, anatomical structures of interest, such as the annulus and the closure line, are detected.

Any representation may be used for identification. For example, the annulus, leaflets, free edges, root, and closure line are represented as fit curves or detected surfaces. Anatomical landmarks may be represented as volume shapes, areas, surfaces, lines, curves, or points.

One or more machine-learnt classifiers are used to identify the anatomic structure or structures. Any of the classifiers discussed above, but trained for locating specific or groups of specific anatomic structure of the valve may be used. The classifier locates the entire structure. Alternatively, different points are sequentially classified. The global valve region is searched point by point. For each point, input features for the point and surrounding points are used to classify the probability that the point is part of the anatomy.

Any of the input features discussed herein may be used, such as using both B-mode and flow mode features. In one embodiment, the input features from fluid response are not used. The input features from B-mode data are used without flow data features. The features for locations within the global region or bounding box are used and features for other locations are not used. Alternatively, features within a window function of the point being classified regardless of position within or not of the bounding box are used.

The features are directional. For example, Haar or steerable features are directional. The orientation of the valve, as reflected in the valve region, is used for calculating or selecting the features. The orientation indicates more likely positioning or relationships of different anatomy. Scale may likewise be used to select or calculate the features. The bounding box parameters are used in feature calculation.

The features are applied to a matrix representing a machine-learnt classifier. In one embodiment, the classifier is a PBT classifier, so provides the target posterior probability. The points with the highest probability, probability over a threshold, or other criteria are selected as representing the anatomy. Points with lesser probabilities are not selected. The classifier outputs the probabilities for each point tested, and the points with the greater or sufficient probability are used as indicating the anatomy.

The detected anatomy may be used as the output. The variance may be great due to the resolution of the data. There may be little direct correlation of the highlighted or detected lines to the B-mode structure shown. Since the valve moves rapidly and is relatively small as compared to the resolution of ultrasound, a patient-specific valve model is fit to the detected anatomy in act 39. A patient-specific valve model is fit to the input data to visualize the valve anatomy and to assist therapy planning and procedure simulation. A model is fit to the detected anatomy of the specific patient, so that the fitting causes the model to be patient-specific. For example, the annulus, leaflets, free edge, root, or other landmarks of the model are fit to the corresponding detected anatomy. In the case of the left heart, valve models may include (1) the aortic annulus, aortic root, leaflets, other landmarks, and/or left ventricle outflow tract or (2) the mitral valve annulus, leaflets, other landmarks, and free edge. Any combination of different anatomy of the valve may be modeled. The fitting results in adjustment (e.g., translation, orientation, and/or scaling) of other anatomy represented in the model to the patient.

Any model of the valve may be used, such as a theoretical or programmed model. In one embodiment, a statistical shape model is used. A statistical shape model of the valve is built from a training set. Any number of samples may be used to determine the position and/or deviation probabilities for the valve anatomy. A mesh, feature collection, sample grid or other distribution is used to represent the model.

The model is labeled. The anatomy is indicated by the model, such as indicating a position of the posterior leaflet, the anterior leaflet, the annulus, and the closure line. The model provides detailed information missing from, not easily viewable, or also included in the data representing the patient. For example, the closure line and annulus are not easily viewable in B-mode images. The model clearly indicates the locations for the closure line and annulus. In alternative embodiments, no labeling is provided.

The model is transformed to become a patient-specific model. The model is altered or fit to patient-specific data. For example, a statistical shape model is transformed using the detected anatomy. The anatomy of the statistical shape model is transformed to fit with detected anatomy. The spatial distribution probabilities of the statistical model may limit the transform so that the anatomy more likely represents the norm or possible arrangements. Given the previously detected anatomy, a patient-specific valve model is constructed to visualize the anatomical structure.

Any fitting may be used. For example, thin-plate-spline, Gaussian bending, non-linear ICP, or other non-rigid transforms are applied. In one embodiment, a number (e.g., 13) of points identified of detected anatomy are selected from both the statistical shape model and the patient anatomy. Rather than using points identified as part of the detection, the detected anatomy may be resampled for the transformation. The selected points are equally spaced along the detected anatomy. These anchor points are used to compute the Thin-Plate-Spline (TPS) transformation, which deforms the valve model (e.g., statistical shape model) non-linearly to fit the detected anatomy. Only some or all of the anatomy of the model are transformed. The fit statistical shape or other model provides the location of the labeled anatomy, surface, or other valve information specific to the patient.

Figure 3:
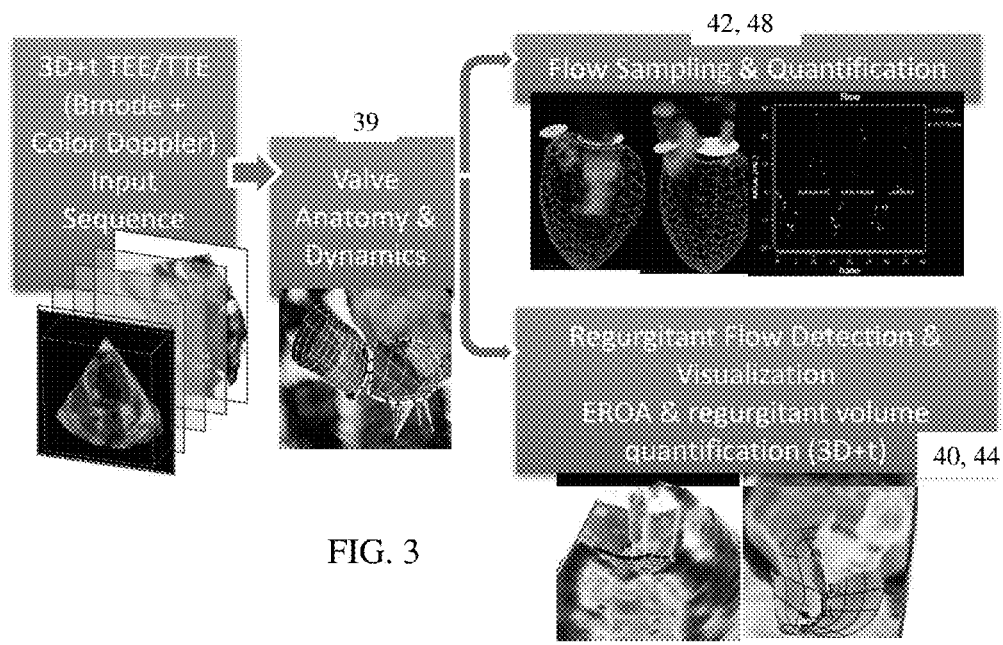
FIG. 3 is a flow chart diagram of another embodiment of a method for detecting a regurgitant orifice in echocardiography.

As shown in FIG. 3, the fit model in the form of a mesh captures the valve anatomy. By fitting the model at different times through a sequence of data or volumes, the dynamic behavior of the valve is captured by the change in the model. The model may incorporate physics or other dynamic behavior to limit change over time.

The fit model for a given time or over time is used to assist or as a basis for assessment. In acts 42 and 48, the model is used to determine where to sample flow for quantification. In acts 40 and 44, the model is used to better detect a regurgitant orifice and/or jet. The model may also be used for visualization to better indicate the valve anatomy at a given time or over time in a sequence of images. The model may be adjusted based on further detection, such as detection of the regurgitant orifice.

In act 42, the processor positions sample planes or locations for calculating one or more flow quantities. Transvalvular flow and/or flow on one side of the valve are calculated. The fit model is used to define the sides of the valve used for calculating. In one embodiment, the fit model is used to define sample planes along which the flow data is sampled for calculating. Planes are derived from on the valve anatomy (e.g., from aortic and mitral annulus) to sample the color Doppler flow image. The planes are based on the anatomical model or models. For example, the transvalvular (on both sides of the valve) flow data is sampled over time or at different times from the flow-mode data. The sampled data is along one or more planes positioned relative to the heart valve. The plane or planes are positioned based on the model at each of the times, so may shift over time.

Figure 4:
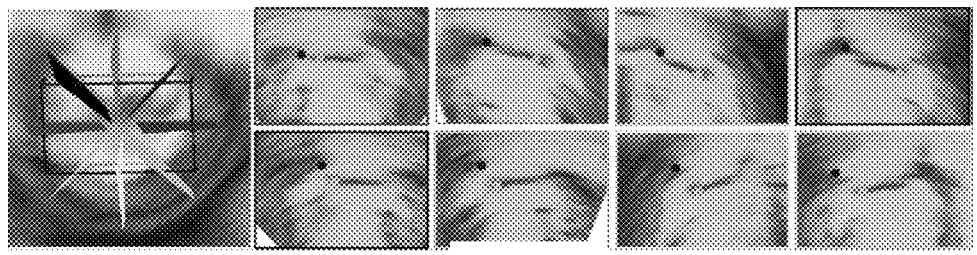
FIG. 4 shows example oriented sampling planes for sampling for dynamic quantification.

FIG. 4 shows an example sampling based on orientation of the valve as indicated by the model. The image on the left shows nine planes defined relative to the orientation of the valve model. Any number of planes with equal or non-equal spacing may be used. Other plane orientations relative to the valve orientation may be used. Starting from a plane at the anterior commissure, a sequence of any number (e.g., 30) constrained sub-volumes V, for the anterior (FIG. 4—upper row) and the posterior (FIG. 4—bottom row) annulus and closure line are used. As an alternative to defining sampling planes, the valve model is used to indicate the direction along which data is sampled or other region (e.g., left ventricle side) for sampling or quantifying.

In act 48, the processor uses the flow-mode data at one time or over time to calculate quantities. The processor computes any quantity. The quantity may be an instantaneous value, such as flow at a given time. For example, differential flow on different sides of the valve is quantified as a difference in average flow. The quantity may be a dynamic flow quantity, such as a value for flow as a function of time. For example, a change in flow on one side over time is calculated. In one embodiment, transvalvular flow is quantified by integrating flow volumes from segmented flow.

Potential aliasing can occur due to blood velocities above the Doppler sampling limit given by the ultrasound probe. This effect is compensated for using aforementioned sampling planes. Dealiasing may be done manually, by changing the sampling scale. Automatic dealiasing based on machine learning may also be performed, where aliased signal is automatically detected using image features, and the sampling scale automatically shifted based on the detected aliasing area.

In act 40, the regurgitant orifice is detected. In order to detect and quantify the regurgitation, it is important to find the location of the valve regurgitant orifice, $L(l_x, l_y, l_z)$, where the abnormal leaking of blood occurs. The regurgitant orifice may be a point, line (e.g., curve) or area (e.g., surface). Locating the regurgitant orifice may be a challenging task due to the limited resolution and low signal-to-noise ratio at the valve region in the echocardiography data. Given the size of the typical regurgitant orifice and resolution of ultrasound data, the regurgitant orifice is a point as represented in the ultrasound data. The model may represent the regurgitant orifice more precisely.

The presence and location of regurgitant areas is detected and/or tracked over time. The origin of regurgitant jets coincide with the valve closure line (e.g., free edge) in systole for the mitral valve and diastole for the aortic valve. Similar timing is provided for right heart valves.

To detect the orifice, learning-based methods are applied using the multi-channel image features derived from both B-mode and color Doppler flow. The processor detects the regurgitant orifice with a machine-learnt classifier. Any of the features discussed above, such as Haar and/or steerable features derived from both B-mode and flow-mode data, may be used. Any of the machine learning techniques and corresponding learnt classifiers may be used, such as PBT or marginal space learning. In response to inputting the feature values, the matrix embodying the classifier outputs a location of the regurgitant orifice or identifies a location with a greatest probability of being the regurgitant orifice.

In one embodiment, a position detector is trained with PBT and 3D multi-channel features (e.g., both features from tissue response and features from fluid response) to form a strong classifier. The trained classifier returns a peak posterior probability at the regurgitant location and a low probability score if there is not regurgitant jet in the image or at the location. To remove outliers, the position of the regurgitant orifice is constrained to be within the global location of the valve anatomy. The constraint optimizes the joint probability. The joint probability is a function of the different machine-learnt classifiers, such as the classifier for detecting the valve and the classifier for detecting the orifice. The joint probability may not be calculated, but the constraint acts to weight the localization of the regurgitant orifice. The resulting probability from the regurgitant orifice classifier is a joint probability (e.g., function of both classifiers).

The detection of the location of the regurgitant orifice uses the valve model as fit for the patient. The detection is a function of the previously derived anatomical model. The machine-learnt classifier is applied based on the model as fit to the valve. One or more approaches relying on the model to assist in finding the orifice may be used.

In one embodiment, the machine-learnt classifier is applied only to locations along a free edge or other specific anatomy designated by the fit model. The model indicates the locations for the given time. The classifier is applied to just those locations to test for the regurgitant orifice. Other locations are not classified.

In another embodiment, the model is used to weight and/or provide separate features input to the classifier. A distance from a location being classified to the valve or specific anatomy of the valve as represented by the fit model is input as a feature. For example, the distance to the free edge is calculated and used in the full feature vector of the classifier. This could be beneficial since sometimes the Doppler jet appears to start above the actual location of the regurgitant orifice due to the spatial resolution of the probe. Distances to multiple portions of the valve model (e.g. commissures, leaflets, and annulus) may be used.

In yet another embodiment, the processor calculates at least some of the input features based on a direction indicated by the fit model of the valve. The model indicates an orientation for anatomy, such as the free edge. The features calculated from the flow may better distinguish orifice from non-orifice along one direction as compared to another direction. Similarly, the tissue features may be more discriminative based on direction. Spatial features aligned with or relative to the valve model are calculated and used for classification. Classification may be stronger when the input features are normalized to the direction since the classifier has to deal with less variation.

The detection of the regurgitant orifice based on the fit model may be iterative and/or include a reverse adjustment. Once the regurgitant orifice is detected, the location may be used to correct discrepancies or uncertainty of the free edge or closure line of the fit model. The free edge or closure line may be based on the model fitting, which is an estimate. Where the regurgitant orifice is determined to be spaced from the free edge or closure line, the model or fit of the model may be adjusted to place the free edge or closure line at the regurgitant orifice. Only this part of the model is altered. Alternatively, the entire fit is altered, such as adjusting other parts of the model based on the adjustment of the free edge or closure line. By altering the model fit or the model based on the regurgitant orifice location, both estimation or detection acts interact to benefit each other.

In act 44, the regurgitant jet is segmented based on the detected regurgitant orifice of the heart valve. For example, the regurgitant orifice is used to segment the mitral regurgitation jet. The detected regurgitant orifice is used as a seed point to segment the jet.

Any process for segmentation may be used. The regurgitant orifice may be associated with a velocity. Any velocities within a range are treated as part of the jet. The resulting spatial distribution may be filtered. In another embodiment, an iso-velocity region is segmented based on the color Doppler data. Because a main characterization of the regurgitation is the reverse blood flow, a random walker algorithm may be used to segment the jet. The direction of regurgitant flow through the valve or valve model is used to indicate on which side of the valve to search for the jet. By incorporating the direction constraint along the regurgitant flow, the random walker locates a volume having the same or similar velocity. The valve model improves accuracy of the regurgitant jet, since flow cannot cross the valve model. Other segmentation may be used.

The regurgitation jet from the segmentation may be quantified. The velocity, a volume, a variance, a distribution, or other quantity is calculated. In one embodiment, an iso-velocity surface with a proximal iso-velocity surface area (PISA) is extracted. A surface associated with a same or similar velocity in the jet is found. For example, the marching cubes algorithm is applied to locate the PISA. The PISA is used to compute the regurgitant volume and the effective regurgitant orifice area (EROA). For example, EROA= (PISA×flow velocity of PISA)/peak velocity of the jet over a cardiac cycle. As another example, the volume is an integration of the PISA×the flow velocity over time. Other quantities may be calculated.

Acts 30-48 are repeated over time. The patient's heart or heart valve is continuously or regularly scanned in act 30. For each complete scan or time, the features are calculated in act 36, the valve located in act 38, and the model fit to the valve in act 39. Based on the model fit for that time or phase of the heart cycle, any regurgitant orifice may be detected in act 40 and the jet segmented in act 44. If the time or phase is not associated with regurgitation for that valve, no orifice is found or the orifice detection is not applied. For each time, the sample planes of act 42 are positioned based on the model fit for that time. The flow is calculated for that time in act 48.

As an alternative or in addition to applying detection of the valve, fitting of the model, and/or detecting the regurgitant orifice at each time, tracking may be used. Speckle or other correlation may indicate a translation, rotation, and/or scaling from one frame of data to the next. By testing different displacements or changes between two frames, the displacement with the greatest correlation or similarity is found, providing tracking of the region, valve, and/or orifice. The model may be fit based on the detected or tracked locations of anatomy. Other tracking may be used, such as learning-based tracking (follow a pre-learned trajectory that is fitted to the data), symmetric registration, belief-propagation, or a mix of the above.

The valve anatomy is detected over time (i.e., at each time) or detected once or periodically and tracked the rest of the time. The valve model is fit to detected and/or tracked anatomy. As a result, a dynamic patient-specific model (i.e., model over time) is determined using both B-Mode and color Doppler.

By repeating detection and/or tracking the regurgitant orifice over time, the jet seed point is determined over time. While the regurgitation may occur only part of the heart cycle, temporal aspects of the regurgitation may be quantified, such as determining the regurgitant volume for a heart cycle and/or the velocity time integral. The seed point (i.e., regurgitant orifice) over time is used to segment the jet at the different times, providing jet information as a function of time. The segmentation is done for all systolic and diastolic phases of the cardiac cycle in case of mitral and aortic valve, respectively. The segmentation for the valves of the right heart is alternatively or additionally performed at the appropriate portions of the heart cycle. The presence and location of the regurgitant orifice is detected and tracked over time. The origin of regurgitant jets coincides with the valve closure line (a.k.a. free edge) in the appropriate heart phase for the valve.

In act 50, an image or quantity is output. The processor outputs to a display, printer, memory, or network. The image is from the acquired scan data and/or from the fit model. For example, a combination image is generated where B-mode data shows tissue, flow data indicates fluid, and a mesh, labels, points, coloration, brightness, or lines from the fit model highlight the valve.

Figure 5:
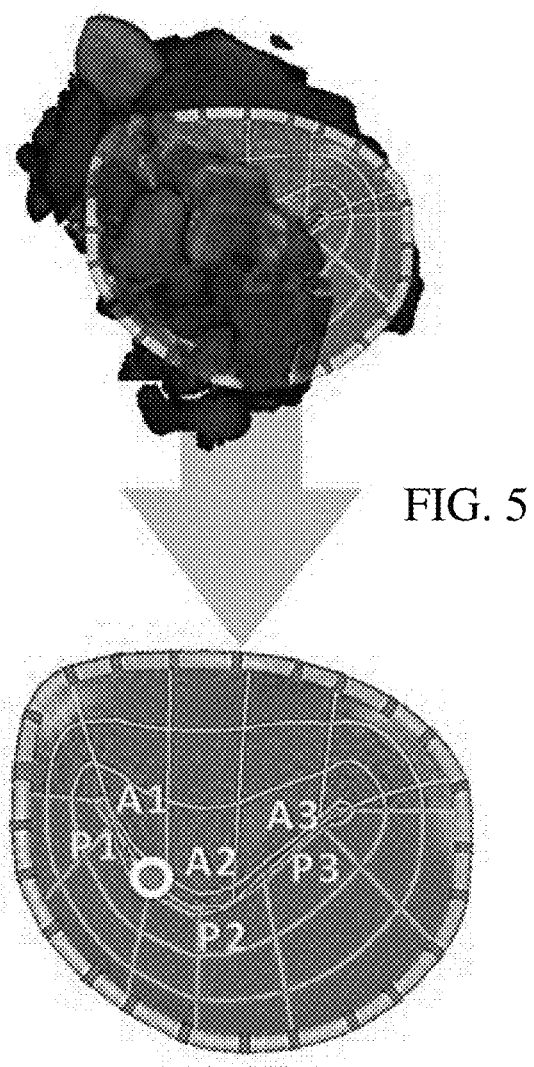
FIG. 5 shows an example of a rendering of a valve model with and without regurgitant jet information.

In one embodiment, an image of the fit model and the regurgitant point is displayed without overlay of the regurgitant jet. The flow associated with the regurgitant jet is clipped or cropped, such as not including any flow between the model and the viewer. The regurgitant jet is not shown in a same representation with the heart valve, at least for part of the display screen. The regurgitant jet with or without the model may be separately rendered for another part of the display screen. The upper portion of FIG. 5 shows a valve model rendered with the color flow information, including from a regurgitant jet. The color information obscures the regurgitant orifice and parts of the valve model. The lower portion shows a rendering of the model with the detected regurgitant orifice, but without the regurgitant jet or without the color overlay for the flow-mode data. Where clinicians are looking for the actual location of the regurgitant orifice on the valve, particularly in which segment (A/P1-3) the orifice occurs, the lower image may be more useful to plan a repair. Viewing the orifice may assist for planning or confirmation of treatment.

The image is a rendering of a three-dimensional volume. Voxels or data representing three-dimensional locations are rendered to a two-dimensional view. Ray casting, projection, surface, or other rendering may be used. The viewing direction is from one side of the valve. Other or multiple viewing directions may be used and chosen interactively by the user. Multi-planar reconstruction may additionally or alternatively be used.

The image includes highlighting. The highlighting is in addition to any gray scale mapped B-mode and/or color mapped flow mode data. The highlighting is a different color, brightness, resolution, graphic, or other characteristic to show a feature more prominently. The highlighting may be a graphic overlay or is an alteration of the data mapped to display values. The highlighting may be of a surface, of a particular anatomy, of a curve, a label, a point, or of other details of the valve. The fitted model indicates the location and/or what to highlight.

The mesh determined by the modeling may be used to surface render the valve. The mesh is an outline or surface, but other outlines, such as interconnected landmarks, may be displayed. In alternative embodiments, the image is of the landmarks or a representation of a valve fit to the mesh or landmarks.

In one embodiment, the model information is overlaid on a rendering of the heart or valves. The valve images are rendered from medical data with a same scale and perspective as an outline overlaid on the rendering. Color coding or other display modulation may be used with or in addition to an overlay. For example, different surfaces of the valve are rendered from B-mode data in gray scale with color modulation specific to the fitted model surface. One surface may be rendered in one color and another in another color. One rendering or multiple renderings from the same volume may be displayed.

The image is generated to represent the valve at one time. A sequence of images may be displayed to represent the valve over time. The sequence is rendered from the different volumes throughout a portion of (e.g., simulating closure) or entire heart cycle.

An image of the regurgitant jet may be generated. The regurgitant jet is shown by the color flow information. In other embodiments, the segmentation is used to further highlight the jet. Rather than using color mapping of velocity alone, locations associated with a mesh, iso-velocity, or detected surface may be highlighted to show the jet with more emphasis relative to other flow. Alternatively, a landmark may be visualized at the jet position and the flow image hidden to simultaneously analyze jet location and B-Mode (anatomy).

Alternatively or additionally, the image displays a value or other quantification. Any of the quantities calculated in act 48, quantities derived from the fitted model, and/or quantities for the regurgitant jet are displayed. For example, clinical biomarkers, such as PISA and EROA, are displayed. Since the segmentation and/or sampling are performed over time, one or more quantities of dynamic function may be output, such as velocity time integral or regurgitant volume.

The quantity is displayed as a number or text. Alternatively, a graph of the quantity as a function of time and/or location is generated. A bar graph or other representation of the quantity may be used. Brightness or color coding with a key relating the brightness or color to the value of the quantity may be used.

The detected regurgitant jet may also be applied to refine the model of the valve. Any part of the model may be refined, such as altering the free-edges. The jet indicates a state of the free edges. If no jet is detected, the model of the valve is forced to be closed since no insufficiency is present. If a jet is detected, the model of the valve is forced to be open. The image or quantity is output based on the refined model.

Figure 6:
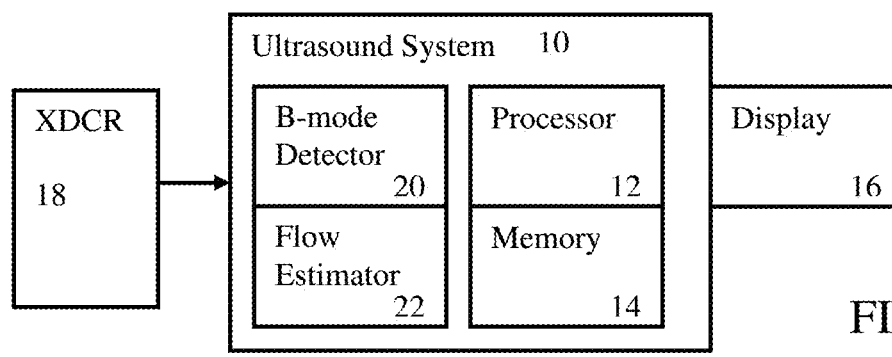
FIG. 6 is a block diagram of one embodiment of a system for detecting a regurgitant orifice.

FIG. 6 shows a system for detecting a regurgitant point. The system includes a transducer 18, an ultrasound scanner 10, and a display 16. The ultrasound scanner 10 includes a B-mode detector 20, a flow estimator 22, a processor 12, and a memory 14. In other embodiments, the system is a workstation, computer, or server for detecting using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for detecting. Additional, different, or fewer components may be used.

The ultrasound scanner 10 includes a transmit beamformer, receive beamformer, B-mode detector 20, flow estimator 22 (e.g., Doppler detector), harmonic response detector, contrast agent detector, scan converter, filter, combinations thereof, or other now known or later developed medical diagnostic ultrasound system components.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension. In another embodiment, the array is a one-dimensional array. Multi-dimensional arrays or a plurality of one-dimensional arrays may be provided.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rocking an array or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart or valve volume. The scan may be repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., Doppler mode), contrast agent, harmonic, or other ultrasound modes of imaging. For valve detection, both B-mode and flow or Doppler mode data are acquired.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart or valve volume. The heart volume includes at least the valve, but other portions of the heart may be represented. The memory 14 stores flow (e.g., velocity, energy or both) and/or B-mode ultrasound data. Alternatively, the medical image data is transferred to the processor 12 from another device. The medical image ultrasound data is a three-dimensional data set or a sequence of such sets. The data represents a three-dimensional region.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging using the data. For example, real-time imaging is provided by generating the images substantially simultaneously with the acquisition of the data by scanning. While scanning to acquire a next or subsequent set of data, an image of a fit model is generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring and/or generating a planar reconstruction without concurrent acquisition.

The memory 14 is additionally or alternatively a non-transitory computer readable storage medium with processing instructions. The memory 14 stores data representing instructions executable by the programmed processor 12 for detecting a regurgitant orifice. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein, such as controlling scanning, calculating features, detecting anatomy, measuring anatomy, and/or controlling imaging.

The processor 12 performs machine learning and/or applies a machine-learnt algorithm. For example, the processor 12 applies a probabilistic model to detect valve anatomy. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different anatomy. The probabilistic models may be joint or dependent. The location of other anatomies or jets is used to limit or define a search space for a current anatomy and/or as a feature input for classification of another anatomy.

The different classifiers are the same or different types of classifiers. The same or different types of classifiers may be used for the same type of classification, such as different types of classifiers being used for different marginal space classification (e.g., the classifier for global translation is different than the classifier for global rotation).

In one embodiment, the probabilistic model is formed from a plurality of probabilistic boosting tree classifiers. Separate training and resulting machine-trained classifiers are provided for different aspects to be detected. For example, separate probabilistic boosting tree classifiers are provided for each of the marginal space types.

For application, the processor 12 calculates features for classification. The same or different features are used for classification in each stage. The features are three-dimensional features. 3D data defined by a window function is used to calculate the features. The window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may determine a desired subset or set of features to be used for a given classification task. Other types of features may alternatively or additionally be used. In one embodiment, the features for locating the anatomy and/or the regurgitant region use both B-mode (e.g., tissue) and flow-mode (e.g., fluid) data.

In one embodiment, the processor 12 is configured to implement one or more of the acts of FIG. 2. In other embodiments, the processor 12 is configured to locate the valve, fit a model to the valve, and use the fit model for further sampling, quantification, and/or regurgitant orifice detection. The detection of the valve anatomy and/or the fitting of the model are performed over time, providing a fit model for each sampled time through all or part of a heart cycle. The processor 12 is configured to use the model to locate a regurgitant region. A classifier may be applied, but the input features and/or locations classified are a function of the fit model for that time. By repeating over time, the regurgitant region over time is located by the processor 12. The processor 12 may use the located regurgitant region to alter the model or model fit.

The locations are determined without user indication of a location of the valve and without user indication of a location on an image. Automatic detection of the orifice is provided.

The processor 12 is configured to generate an image. The fit model, identified anatomy, located orifice, or other information (e.g., mesh locations or quantities) is used to generate the image. The patient-specific scan data may be used for imaging. The image provides a visualization of the valve. The visualization may be of the valve prior to treatment or may be of the valve after treatment. The image may or may not include the regurgitant jet.

The display 16 is a CRT, LCD, plasma, projector, printer, or other output device for showing an image. The display 16 displays an image of the detected anatomy, such as an image of a valve rendered from medical data and overlaid or highlighted based on the fit model. The display 16 generates a visualization of the valve with highlighting. The highlighting is color, brightness, or other modification to show the regurgitant orifice, valve, valve anatomy, and/or regurgitant jet. A sequence of images representing the valve and/or orifice over time may be displayed.

The visualization may be generated during a same examination session as the scan. The detected anatomy may or may not be segmented, such as just displaying the valve and/or jet. Alternatively or additionally, the displayed valve may be based on the statistical model, so be different than the anatomy or scan data alone. A value of a measurement may be displayed. The value may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for detecting a regurgitant point in echocardiography, the method comprising:
   detecting, by a processor, a valve with a first machine-learnt classifier using input first features from both B-mode and flow-mode data for a patient;
   fitting, by the processor, a model of the valve to the detected valve of the patient;
   detecting, by the processor, the regurgitant point with a second machine-learnt classifier using second features from both the B-mode and the flow-mode data, the second machine-learnt classifier being applied only to locations along a free edge of the model as fit to the valve;
   segmenting, by the processor, regurgitant jet image data of a regurgitant jet using the regurgitant point as a seed point; and
   outputting an image including the B-mode data, the flow-mode data, the model as fit to the valve, and the regurgitant jet image data as segmented.

2. The method of claim 1 wherein detecting the valve comprises detecting a location, orientation, and scale of the valve represented by the B-mode data.

3. The method of claim 1 wherein fitting the model comprises fitting an annulus, leaflets, free edge, or combinations thereof.

4. The method of claim 1 wherein fitting the model comprises transforming a statistical shape model as a function of the detected valve.

5. The method of claim 1 wherein detecting with the first and second machine-learnt classifiers comprises calculating Haar, steerable, or Haar and steerable feature values for the B-mode data and for the flow-mode data.

6. The method of claim 1 further comprising calculating the quantity from sample planes positioned relative to the detected valve.

7. The method of claim 1 wherein segmenting comprises applying a random walker for the flow-mode data while using the regurgitant point to spatially limit the segmentation of the regurgitant jet.

8. The method of claim 1 wherein outputting further comprises outputting a quantity as representing the regurgitant jet.

9. The method of claim 1 further comprising repeating the detecting the valve, fitting, detecting the regurgitant point, and segmenting for different times in a cardiac cycle.

10. The method of claim 1 further comprising:
    scanning, with a transducer adjacent the patient, a cardiac region of the patient with ultrasound;
    detecting, with a B-mode detector and in response to the scanning, the B-mode data representing tissue in the cardiac region;
    estimating, with a flow estimator and in response to the scanning, the flow-mode data representing fluid in the cardiac region, the flow-mode data comprising energy, velocity, or energy and velocity.

11. The method of claim 1 wherein detecting the valve comprises constraining the model as fit to the valve or part of the model as fit to the valve to locations without flow-mode data.

12. In a non-transitory computer readable storage medium having stored therein data representing instructions executable by a programmed processor for detecting a regurgitant orifice, the storage medium comprising instructions for:

detecting, at different times, anatomy of a heart valve from first features derived from both B-mode and color flow Doppler data;

sampling, at the different times, transvalvular flow over time from the color flow Doppler data on sampling planes positioned relative to the detected heart valves for the different times;

calculating a quantity of transvalvular flow from the sampling;

fitting a model of the heart valve to the detected anatomy of the heart valve;

detecting the regurgitant orifice from second features from both the color flow Doppler data and from the B-mode data, by applying a machine-learnt classifier only to locations along a free edge of the model as fit to the heart valve;

segmenting a regurgitant jet for the heart valve using the regurgitant orifice as a seed point; computing a clinical biomarker for the regurgitant jet; and providing a visualization of the anatomy of the heart valve including the clinical biomarker and the quantity of transvalvular flow.

13. The non-transitory computer readable storage medium of claim 12 wherein detecting the anatomy comprises detecting aortic, mitral, pulmonary, or tricuspid anatomy.

14. The non-transitory computer readable storage medium of claim 12 further comprising computing dynamic flow quantity for flow as a function of time from the sampling.

15. The non-transitory computer readable storage medium of claim 12 further comprising displaying the model as fit to the heart valve and the regurgitant orifice without the regurgitant jet.

16. A system for detecting a regurgitant region, the system comprising:

an ultrasound scanner configured to scan a heart volume of a patient, the scan providing B-mode and Doppler flow data;

a processor configured to fit a model of a heart valve over time to the B-mode data using the B-mode data and the Doppler flow data, and use the model as fit to the heart valve to locate the regurgitant region over time by applying a machine-learnt classifier only to locations along a free edge of the model as fit to the heart valve; and a display configured to generate a visualization of the model as fit to the heart valve over time and highlight the regurgitant region without displaying flow data for a regurgitant jet.

* * * * *